US009387091B2

(12) United States Patent
Garner et al.

(10) Patent No.: US 9,387,091 B2
(45) Date of Patent: Jul. 12, 2016

(54) SPINAL FUSION IMPLANT

(71) Applicant: DePuy Synthes Products, Inc., Raynham, MA (US)

(72) Inventors: Ronald Garner, Hull, MA (US); Sara Dziedzic, North Attleboro, MA (US); Michael Mahoney, Middletown, RI (US); Ramon A. Ruberte, Durham, NC (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/574,441

(22) Filed: Dec. 18, 2014

(65) Prior Publication Data
US 2015/0105860 A1    Apr. 16, 2015

Related U.S. Application Data

(63) Continuation of application No. 14/053,821, filed on Oct. 15, 2013, now Pat. No. 8,936,643, which is a continuation of application No. 13/230,163, filed on Sep. 12, 2011, now Pat. No. 8,579,983, which is a continuation of application No. 11/496,564, filed on Jul. 31, 2006, now Pat. No. 8,034,110.

(51) Int. Cl.
*A61F 2/44* (2006.01)
*A61F 2/46* (2006.01)
(Continued)

(52) U.S. Cl.
CPC ............... *A61F 2/4465* (2013.01); *A61F 2/442* (2013.01); *A61F 2/447* (2013.01); *A61F 2/4455* (2013.01);
(Continued)

(58) Field of Classification Search
CPC ....... A61F 2/44; A61F 2/4465; A61F 2/4611; A61F 2/4455
USPC .......................... 623/17.11–17.16; 606/86 A
See application file for complete search history.

(56) References Cited

U.S. PATENT DOCUMENTS 2,115,250 A    4/1938  Bruson
2,170,111 A    8/1939  Bruson
(Continued)

FOREIGN PATENT DOCUMENTS

WO    93/17669 A1    9/1993
WO    97/26847 A1    7/1997
(Continued)

OTHER PUBLICATIONS

Supplementary European Search Report for Application No. 07836359.5, dated Aug. 29, 2011.
(Continued)

*Primary Examiner* — Christopher Beccia
(74) *Attorney, Agent, or Firm* — Nutter McClennen & Fish LLP

(57) ABSTRACT

The present invention provides a device and methodology for use in spinal fusion surgeries. An implant is proved for forming a rigid structure between adjoining vertebrae in a patient. The implant is a cage defined by at least a first end, second end, first side, and second side surface, wherein first and second side surfaces extend substantially parallel to each other to span a space between adjoining vertebrae and first and second ends interconnect said first side surface and second side surface. The cage incorporates one or more flexible joints that allow the cage to be deformed for insertion into a patient. The ability to deform the cage allows a greater ease and flexibility in inserting and positioning the implant.

21 Claims, 12 Drawing Sheets

(51) Int. Cl.
*A61F 2/28* (2006.01)
*A61F 2/30* (2006.01)

(52) U.S. Cl.
CPC ....... *A61F 2/4611* (2013.01); *A61F 2002/2835* (2013.01); *A61F 2002/30133* (2013.01); *A61F 2002/30383* (2013.01); *A61F 2002/30471* (2013.01); *A61F 2002/30538* (2013.01); *A61F 2002/30571* (2013.01); *A61F 2002/30579* (2013.01); *A61F 2002/30784* (2013.01); *A61F 2002/4415* (2013.01); *A61F 2002/4635* (2013.01); *A61F 2220/0025* (2013.01); *A61F 2220/0091* (2013.01); *A61F 2230/0015* (2013.01); *A61F 2230/0095* (2013.01); *A61F 2250/0004* (2013.01); *A61F 2250/0006* (2013.01)

(56) References Cited

U.S. PATENT DOCUMENTS

| | | | |
|---|---|---|---|
| 2,229,024 | A | 1/1941 | Bruson |
| 2,706,701 | A | 4/1955 | Beller et al. |
| 2,710,277 | A | 6/1955 | Shelanski et al. |
| 2,826,532 | A | 3/1958 | Hosmer |
| 2,900,305 | A | 8/1959 | Siggia |
| 2,977,315 | A | 3/1961 | Scheib et al. |
| 3,228,828 | A | 1/1966 | Romano |
| 3,717,655 | A | 2/1973 | Godefroi et al. |
| 4,352,883 | A | 10/1982 | Lim |
| 4,440,921 | A | 4/1984 | Allcock et al. |
| 4,495,174 | A | 1/1985 | Allcock et al. |
| 4,645,503 | A | 2/1987 | Lin et al. |
| 4,743,256 | A | 5/1988 | Brantigan |
| 4,772,287 | A | 9/1988 | Ray et al. |
| 4,834,757 | A | 5/1989 | Brantigan |
| 4,863,476 | A | 9/1989 | Shepperd |
| 4,871,366 | A | 10/1989 | von Recum et al. |
| 4,878,915 | A | 11/1989 | Brantigan |
| 4,880,622 | A | 11/1989 | Allcock et al. |
| 5,059,193 | A | 10/1991 | Kuslich |
| 5,133,755 | A | 7/1992 | Brekke |
| 5,192,327 | A | 3/1993 | Brantigan |
| 5,390,683 | A | 2/1995 | Pisharodi |
| 5,397,364 | A | 3/1995 | Kozak et al. |
| 5,410,016 | A | 4/1995 | Hubbell et al. |
| 5,425,772 | A | 6/1995 | Brantigan |
| 5,443,514 | A | 8/1995 | Steffee |
| 5,522,895 | A | 6/1996 | Mikos |
| 5,522,899 | A | 6/1996 | Michelson |
| 5,549,679 | A | 8/1996 | Kuslich |
| 5,554,191 | A | 9/1996 | Lahille |
| 5,562,736 | A | 10/1996 | Ray et al. |
| 5,658,335 | A | 8/1997 | Allen |
| 5,665,122 | A | 9/1997 | Kambin |
| 5,679,723 | A | 10/1997 | Cooper et al. |
| 5,702,449 | A | 12/1997 | McKay |
| 5,716,415 | A | 2/1998 | Steffee |
| 5,782,832 | A | 7/1998 | Larsen et al. |
| 5,800,549 | A | 9/1998 | Bao et al. |
| 5,807,327 | A | 9/1998 | Green et al. |
| 5,824,084 | A | 10/1998 | Muschler |
| 5,833,657 | A | 11/1998 | Reinhardt et al. |
| 5,837,752 | A | 11/1998 | Shastri et al. |
| 5,860,973 | A | 1/1999 | Michelson |
| 5,865,848 | A | 2/1999 | Baker |
| 5,888,220 | A | 3/1999 | Felt et al. |
| 5,888,227 | A | 3/1999 | Cottle |
| 5,972,385 | A | 10/1999 | Liu et al. |
| 5,984,922 | A | 11/1999 | McKay |
| 5,985,307 | A | 11/1999 | Hanson et al. |
| 6,039,761 | A | 3/2000 | Li et al. |
| 6,045,579 | A | 4/2000 | Hochshuler et al. |
| 6,071,982 | A | 6/2000 | Wise et al. |
| 6,113,624 | A | 9/2000 | Bezwada et al. |
| 6,113,638 | A | 9/2000 | Williams et al. |
| 6,126,689 | A | 10/2000 | Brett |
| 6,129,763 | A | 10/2000 | Chauvin et al. |
| 6,147,135 | A | 11/2000 | Yuan et al. |
| 6,165,486 | A | 12/2000 | Marra et al. |
| 6,171,610 | B1 | 1/2001 | Vacanti et al. |
| 6,176,882 | B1 | 1/2001 | Biedermann et al. |
| 6,187,048 | B1 | 2/2001 | Milner et al. |
| 6,193,757 | B1 | 2/2001 | Foley et al. |
| 6,197,325 | B1 | 3/2001 | MacPhee et al. |
| 6,203,565 | B1 | 3/2001 | Bonutti et al. |
| 6,206,923 | B1 | 3/2001 | Boyd et al. |
| 6,214,368 | B1 | 4/2001 | Lee et al. |
| 6,224,631 | B1 | 5/2001 | Kohrs |
| 6,224,894 | B1 | 5/2001 | Jamiolkowski et al. |
| 6,245,108 | B1 | 6/2001 | Biscup |
| 6,248,131 | B1 | 6/2001 | Felt et al. |
| 6,264,695 | B1 | 7/2001 | Stoy |
| 6,277,149 | B1 | 8/2001 | Boyle et al. |
| 6,280,474 | B1 | 8/2001 | Cassidy et al. |
| 6,306,177 | B1 | 10/2001 | Felt et al. |
| 6,325,827 | B1 | 12/2001 | Lin |
| 6,331,312 | B1 | 12/2001 | Lee et al. |
| 6,332,894 | B1 | 12/2001 | Stalcup et al. |
| 6,368,325 | B1 | 4/2002 | McKinley et al. |
| 6,368,351 | B1 | 4/2002 | Glenn et al. |
| 6,375,682 | B1 | 4/2002 | Fleischmann et al. |
| 6,387,130 | B1 | 5/2002 | Stone et al. |
| 6,413,278 | B1 | 7/2002 | Marchosky |
| 6,436,140 | B1 | 8/2002 | Liu et al. |
| 6,494,883 | B1 | 12/2002 | Ferree |
| 6,533,818 | B1 | 3/2003 | Weber et al. |
| 6,558,424 | B2 | 5/2003 | Thalgott |
| 6,562,072 | B1 | 5/2003 | Fuss et al. |
| 6,562,074 | B2 | 5/2003 | Gerbec et al. |
| 6,582,431 | B1 | 6/2003 | Ray |
| 6,592,625 | B2 | 7/2003 | Cauthen |
| 6,595,998 | B2 | 7/2003 | Johnson et al. |
| 6,610,094 | B2 | 8/2003 | Husson |
| 6,632,235 | B2 | 10/2003 | Weikel et al. |
| 6,669,732 | B2 | 12/2003 | Serhan et al. |
| 6,676,703 | B2 | 1/2004 | Biscup |
| 6,689,132 | B2 * | 2/2004 | Biscup .................. A61F 2/4611 606/279 |
| 6,719,794 | B2 | 4/2004 | Gerber et al. |
| 6,805,697 | B1 | 10/2004 | Helm et al. |
| 6,833,006 | B2 | 12/2004 | Foley et al. |
| 6,835,208 | B2 | 12/2004 | Marchosky |
| 6,974,480 | B2 | 12/2005 | Messerli et al. |
| 6,979,352 | B2 | 12/2005 | Reynolds |
| 7,326,248 | B2 | 2/2008 | Michelson |
| 7,500,991 | B2 | 3/2009 | Bartish, Jr. et al. |
| 7,503,920 | B2 | 3/2009 | Siegal |
| 7,517,363 | B2 | 4/2009 | Rogers et al. |
| 7,520,900 | B2 | 4/2009 | Trieu |
| 7,575,580 | B2 | 8/2009 | Lim et al. |
| 7,655,010 | B2 | 2/2010 | Serhan et al. |
| 7,666,266 | B2 | 2/2010 | Izawa et al. |
| 7,670,374 | B2 | 3/2010 | Schaller |
| 7,785,368 | B2 | 8/2010 | Schaller |
| 7,799,083 | B2 | 9/2010 | Smith et al. |
| 7,918,874 | B2 | 4/2011 | Siegal |
| 7,935,051 | B2 | 5/2011 | Miles et al. |
| 7,942,903 | B2 | 5/2011 | Moskowitz et al. |
| 8,007,535 | B2 | 8/2011 | Hudgins et al. |
| 8,034,110 | B2 | 10/2011 | Garner et al. |
| 8,057,544 | B2 | 11/2011 | Schaller |
| 8,206,423 | B2 | 6/2012 | Siegal |
| 8,343,193 | B2 | 1/2013 | Johnson et al. |
| 8,382,842 | B2 | 2/2013 | Greenhalgh et al. |
| 8,403,990 | B2 | 3/2013 | Dryer et al. |
| 8,454,617 | B2 | 6/2013 | Schaller et al. |
| 8,579,981 | B2 | 11/2013 | Lim et al. |
| 8,579,983 | B2 | 11/2013 | Garner et al. |
| 8,845,734 | B2 | 9/2014 | Weiman |
| 8,900,307 | B2 | 12/2014 | Hawkins et al. |
| 8,926,704 | B2 | 1/2015 | Glerum et al. |
| 8,936,643 | B2 | 1/2015 | Garner et al. |
| 2001/0039452 | A1 | 11/2001 | Zucherman et al. |

(56) References Cited

U.S. PATENT DOCUMENTS

| | | |
|---|---|---|
| 2001/0039453 A1 | 11/2001 | Gresser et al. |
| 2002/0029084 A1 | 3/2002 | Paul et al. |
| 2002/0045904 A1 | 4/2002 | Fuss et al. |
| 2002/0055781 A1 | 5/2002 | Sazy |
| 2002/0058947 A1 | 5/2002 | Hochschuler et al. |
| 2002/0077701 A1 | 6/2002 | Kuslich |
| 2002/0107573 A1 | 8/2002 | Steinberg |
| 2002/0173796 A1 | 11/2002 | Cragg |
| 2002/0193883 A1 | 12/2002 | Wironen |
| 2002/0198526 A1 | 12/2002 | Shaolian et al. |
| 2003/0028251 A1 | 2/2003 | Mathews |
| 2003/0093153 A1 | 5/2003 | Banick et al. |
| 2003/0135275 A1 | 7/2003 | Garcia et al. |
| 2003/0139812 A1 | 7/2003 | Garcia et al. |
| 2004/0002761 A1 | 1/2004 | Rogers et al. |
| 2004/0049270 A1 | 3/2004 | Gewirtz |
| 2004/0087947 A1 | 5/2004 | Lim et al. |
| 2004/0116997 A1 | 6/2004 | Taylor et al. |
| 2004/0127990 A1 | 7/2004 | Bartish et al. |
| 2004/0167538 A1* | 8/2004 | Gerber ............... A61B 17/1671 606/99 |
| 2004/0220669 A1 | 11/2004 | Studer |
| 2004/0230309 A1 | 11/2004 | DiMauro et al. |
| 2005/0019365 A1 | 1/2005 | Frauchiger et al. |
| 2005/0119752 A1 | 6/2005 | Williams et al. |
| 2005/0261682 A1 | 11/2005 | Ferree |
| 2006/0036273 A1 | 2/2006 | Siegal |
| 2006/0041258 A1 | 2/2006 | Galea |
| 2006/0122701 A1 | 6/2006 | Kiester |
| 2006/0129244 A1 | 6/2006 | Ensign |
| 2006/0142858 A1 | 6/2006 | Colleran et al. |
| 2006/0235426 A1 | 10/2006 | Lim et al. |
| 2007/0067035 A1* | 3/2007 | Falahee ............... A61F 2/4455 623/17.11 |
| 2007/0178222 A1 | 8/2007 | Storey et al. |
| 2008/0058933 A1 | 3/2008 | Garner et al. |
| 2008/0188945 A1 | 8/2008 | Boyce et al. |
| 2008/0221586 A1 | 9/2008 | Garcia-Bengochea et al. |
| 2009/0216234 A1 | 8/2009 | Farr et al. |
| 2010/0076502 A1 | 3/2010 | Guyer et al. |
| 2011/0029083 A1 | 2/2011 | Hynes et al. |
| 2011/0029085 A1 | 2/2011 | Hynes et al. |
| 2011/0098818 A1 | 4/2011 | Brodke et al. |
| 2011/0125266 A1 | 5/2011 | Rodgers et al. |
| 2011/0319898 A1 | 12/2011 | O'Neil et al. |
| 2011/0319998 A1 | 12/2011 | O'Neil et al. |
| 2011/0320000 A1 | 12/2011 | O'Neil et al. |
| 2011/0320002 A1 | 12/2011 | Garner et al. |
| 2012/0310352 A1 | 12/2012 | DiMauro et al. |
| 2013/0190875 A1 | 7/2013 | Shulock et al. |
| 2014/0052259 A1 | 2/2014 | Garner et al. |
| 2014/0277481 A1 | 9/2014 | Lee et al. |
| 2015/0094812 A1 | 4/2015 | Cain |
| 2015/0105860 A1 | 4/2015 | Garner et al. |
| 2015/0112437 A1 | 4/2015 | Davis et al. |
| 2015/0164655 A1 | 6/2015 | DiMauro |
| 2015/0173914 A1 | 6/2015 | DiMauro et al. |
| 2015/0196401 A1 | 7/2015 | DiMauro et al. |
| 2015/0202052 A1 | 7/2015 | DiMauro |
| 2015/0216673 A1 | 8/2015 | DiMauro |
| 2015/0265419 A1 | 9/2015 | Garner et al. |
| 2016/0000577 A1 | 1/2016 | DiMauro |

FOREIGN PATENT DOCUMENTS

| | | |
|---|---|---|
| WO | 98/34568 A1 | 8/1998 |
| WO | 99/02214 A1 | 1/1999 |
| WO | 02/17825 A2 | 3/2002 |
| WO | 03/002021 A2 | 1/2003 |
| WO | 03/005937 A1 | 1/2003 |
| WO | 2005/077288 A1 | 8/2005 |
| WO | 2010/075555 A2 | 7/2010 |
| WO | 2012/027490 A2 | 3/2012 |

OTHER PUBLICATIONS

International Search Report and Written Opinion for Application No. PCT/US07/17100, dated Aug. 11, 2008.

International Preliminary Report on Patentability for Application No. PCT/US07/17100, issued Feb. 3, 2009 (9 pages).

[No Author Listed] FDA Approves Cambridge Scientific, Inc.'s Orthopedic WISORB (TM) Malleolar Screw [online], Jul. 30, 2002, 5 pages. Retrieved from the Internet <URL: http://www.cambridgescientificinc.com/interbody.htm>, [retrieved on Oct. 14, 2003].

[No Author Listed] Longer BAK/L Sterile Interbody Fusion Devices. Date believed to be 1997. Product Data Sheet. Zimmer. Retrieved Jul. 23, 2012 from <http://catalog.zimmer.com/content/zpc/products/600/600/620/S20/S045.html>. 2 pages.

[No Author Listed] OSTEOSET® DBM Pellets (Important Medical Information) [online], Nov. 2002, 5 pages. Retrieved from the Internet <URL: http://www.wmt.com/Literature>, [retrieved on Oct. 14, 2003].

[No Author Listed] Sonic Accelerated Fracture Healing System/Exogen 3000. Premarket Approval, U.S. Food & Drug Administration. Date believed to be May 10, 2000, 4 pages. Retrieved Jul. 23, 2012 from <http://www.accessdata.fda.gov/scripts/cdrh/cfdocs/cfPMA/pma.cfm?id=14736#>.

Barakat et al., 1996.

Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.

Bruder et al., Monoclonal antibodies reactive with human osteogenic cell surface antigens. Bone. Sep. 1997;21(3):225-235.

Burkoth et al., A review of photocrosslinked polyanhydrides: in situ forming degradable networks. Biomaterials. Dec. 2000;21(23):2395-2404.

Cheng, B.C., Ph.D., Biomechanical pullout strength and histology of Plasmapore® XP coated implants: Ovine multi time point survival study. Aesculap Implant Systems, LLC, 2013, 12 pages.

Domb, 1996.

Flemming et al., Monoclonal anitbody against adult marrow-derived mesenchymal stem cells recognizes developing vasculature in embryonic human skin. Developmental Dynamics. 1998;212:119-132.

Gennaro, A.R., ed., Remington: The Science and Practice of Pharmacy. Williams & Wilkins, 19th edition, Jun. 1995.

Haas, Norbert P., New Products from AO Development [online], May 2002, 21 pages. Retrieved from the Internet <URL:http://www.ao.asif.ch/development/pdf_tk_news_02.pdf>, [retrieved on Oct. 14, 2003].

Hao et al., Investigation of nanocomposites based on semi-interpenetrating network of [L-poly (epsilon-caprolactone)]/[net-poly (epsilon-caprolactone)] and hydroxyapatite nanocrystals. Biomaterials. Apr. 2003;24(9):1531-9.

Haynesworth et al., Cell surface antigens on human marrow-derived mesenchymal cells are detected by monoclonal antibodies. Bone. 1992;13(1):69-80.

Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.

Invitation to Pay Additional Fees mailed Aug. 10, 2004 for Application No. PCT/US2004/004284 (8 Pages).

International Search Report and Written Opinion mailed Oct. 29, 2004 for Application No. PCT/US2004/004284 (17 Pages).

International Preliminary Report on Patentability mailed Feb. 15, 2005 for Application No. PCT/US2004/004284 (8 Pages).

Kandziora, Frank, et al., "Biomechanical Analysis of Biodegradable Interbody Fusion Cages Augmented with Poly (propylene Glycol-co-Fumaric Acid)," SPINE, 27(15): 1644-1651 (2002).

Kotsias, A., Clinical trial of titanium-coated PEEL cages anterior cervical discectomy and fusion. [Klinishe Untersuching zum Einsatz von titanbeschichteten Polyetheretherketon-Implantaten bei der cervikalen interkorporalen fusion]. Doctoral thesis. Department of Medicine, Charite, University of Medicine Berlin, 2014, 73 pages.

(56) References Cited

OTHER PUBLICATIONS

German language document. English Abstract Only. Kricheldorf and Kreiser-Saunders, 1996.

Kroschwitz et al., eds., Hydrogels. Concise Encyclopedia of Polymer Science and Engineering. Wiley and Sons, pp. 458-459, 1990.

Lange, A.L, Lange's Handbook of Chemistry. McGraw-Hill Inc., 13th edition, Mar. 1985.

Lendlein et al., AB-polymer networks based on oligo(epsilon-caprolactone) segments showing shape-memory properties. Proc Natl Acad Sci U S A. Jan. 30, 2001;98(3):842-7. Epub Jan. 23, 2001.

Malberg, M.I., MD; Pimenta, L., MD; Millan, M.M., MD, 9th International Meeting on Advanced Spine Techniques, May 23-25, 2002, Montreux, Switzerland. Paper #54, Paper #60, and E-Poster #54, 5 pages.

Massia and Hubbell, 1991.

McAfee et al., Minimally invasive anterior retroperitoneal approach to the lumbar spine: Emphasis on the lateral BAK. SPINE 1998;23(13):1476-84.

Mendez et al., Self-curing acrylic formulations containing PMMA/PCL composites: properties and antibiotic release behavior. J Biomed Mater Res. Jul. 2002;61(1):66-74.

New Zealander Office Action issued Jul. 9, 2007 for Application No. 541626 (3 Pages).

Regan et al., Endoscopic thoracic fusion cage. Atlas of Endoscopic Spine Surgery. Quality Medical Publishing, Inc. 1995;350-354.

Slivka et al., In vitro compression testing of fiber-reinforced, bioabsorbable, porous implants. Synthetic Bioabsorbable Polymers for Implants. STP1396, pp. 124-135, ATSM International, Jul. 2000.

Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.

Timmer et al., In vitro degradation of polymeric networks of poly(propylene fumarate) and the crosslinking macromer poly(propylene fumarate)-diacrylate. Biomaterials. Feb. 2003;24(4):571-7.

United States Disctrict Court, Central District of California, Case No. 1:10-CV-00849-LPS, *Nuvasive, Inc.*, vs., *Globus Medical, Inc.*, Videotaped Deposition of: Luiz Pimenta, M.D., May 9, 2012, 20 pages.

Walsh et al., Preparation of porous composite implant materials by in situ polymerization of porous apatite containing epsilon-caprolactone or methyl methacrylate. Biomaterials. Jun. 2001;22(11):1205-12.

\* cited by examiner

SPINAL FUSION IMPLANT

CROSS-REFERENCE TO RELATED APPLICATIONS

This application is a continuation of U.S. patent application Ser. No. 14/053,821, filed Oct. 15, 2013, which is a continuation of U.S. patent application Ser. No. 13/230,163, filed Sep. 12, 2011, now issued as U.S. Pat. No. 8,579,983 on Nov. 12, 2013, titled "SPINAL FUSION IMPLANT," which is a continuation of and claims priority to and the benefit of U.S. patent application Ser. No. 11/496,564, titled "SPINAL FUSION IMPLANT", which was filed on Jul. 31, 2006, now issued as U.S. Pat. No. 8,034,110 on Oct. 11, 2011. The above-identified applications are hereby incorporated by reference in their entirety as though fully set forth herein.

FIELD OF THE INVENTION

The present invention relates to a spinal implant, the accompanying instrumentation and the method of use of both. More particularly, the present invention relates to a device and instrumentation for use in a minimally invasive vertebral fusion procedure.

BACKGROUND OF THE INVENTION

Spinal fusion surgeries that use bone graft material to promote specific vertebrae to grow together into a solid and stable construct are a common method of treating patients with severe back pain. In posterior lumbar interbody fusion (PLIF), damaged disk material is removed and one or more implants are inserted posteriorly to promote bone growth from vertebral body to vertebral body to bridge the gap left by the removed material.

A larger implant better fills the intervertibral space and distributes compressive loads. A larger implant also reduces the need for multiple implants, which may require multiple approaches to insertion and placement. However, Minimally Invasive Surgery (MIS) necessitates the use of less invasive techniques that use smaller access portals to perform the fusion that limit the size of implant that can be used.

An example of this is Transforaminal Posterial Lumbar Interbody Fusion (T-PLIF), which is a variation of the PLIF technique. In this procedure, an implant is inserted through a unilateral or bilateral posterior approach. The T-PLIF technique avoids damage to the nerve structures such as the dura, cauda equine, and the nerve root, but the transforaminal window through which the procedure is performed is limited making the insertion and positioning of the implant difficult.

Thus what is needed is an implant that can suitably fill the intervertebral space but can be inserted and positioned through a small access portal, such as the transforaminal window used in a T-PLIF procedure.

SUMMARY OF THE INVENTION

The present invention provides a device and methodology for use in spinal fusion surgeries. An implant, instrumentation, and methodology are provided for forming a rigid structure between adjoining vertebrae in a patient. The implant is a cage defined by at least a first end, second end, first side, and second side surface. The cage incorporates one or more flexible joints that allow the cage to be deformed for insertion into a patient. The ability to deform the cage allows a greater ease and flexibility in inserting and positioning the implant. For example, a larger implant can to be used in minimally invasive surgery (MIS) techniques because the cage can be transformed to a smaller profile to pass through the smaller access ports used in minimally invasive surgery.

In accordance with one aspect of the present invention, an implant is provided for forming a rigid structure between adjoining vertebrae in a patient. The implant includes a cage defined by at least a first end, second end, first side, and second side surface, and one or more flexible joints incorporated into the cage allowing the cage to be deformed for insertion into a patient.

In certain embodiments, the implant further comprises surface configurations on at least one of the first and second side surfaces of the cage for slidably attaching the implant to an insertion guide. The one or more flexible joints of the implant allow the cage to conform to the shape of the insertion guide as the implant is slid along the length of the guide.

In accordance with another aspect of the present invention, a method is provided for fusing vertebrae of a patient. The method involves the steps of providing an implant of the present invention, and inserting the implant into the space between adjoining vertebrae in a patient to form a rigid structure between the adjoining vertebrae.

In accordance with another embodiment, a system is proved for forming a rigid structure between adjoining vertebrae in a patient. The system includes an implant of the present invention having surface configurations on at least one of the first and second side surfaces of the cage for slidably attaching the implant to an insertion guide; and an insertion guide configured to interface with the surface configurations of the implant for positioning the implant during insertion.

In accordance with another aspect of the present invention, a method is provided for fusing vertebrae of a patient. The method involves providing a system of the present invention comprising a implant with surface configurations and an insertion guide; inserting the insertion guide into the space between adjoining vertebrae in the patient; and sliding the implant along the length of the insertion guide to position the implant in the space between adjoining vertebrae, wherein the implant is slidably attached to the insertion guide by the surface configurations.

BRIEF DESCRIPTION OF THE FIGURES

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions

DETAILED DESCRIPTION OF THE INVENTION

The present invention provides an improved surgical implant and method for performing spinal fusion surgery in a patient. The implant comprises a cage having one or more flexible joints. The cage is defined by at least a first end, second end, first side, and second side surface. The first and second side surfaces extend substantially parallel to each other to span a space between adjoining vertebrae and the first and second ends interconnect the first side surface and the second side surface. The one or more flexible joints allow the cage to be deformed for insertion into a patient. The ability to deform the cage allows a greater ease and flexibility in inserting and positioning the implant. For example, a larger implant can to be used in minimally invasive surgery (MIS) techniques because the cage can be transformed to a smaller profile to pass through the smaller access ports used in minimally invasive surgery. In certain embodiments the implant may further have surface configurations for slidably attaching the implant to a guide used to insert the implant. Embodiments of the implant and methods of use are described below.

Figure 1A:
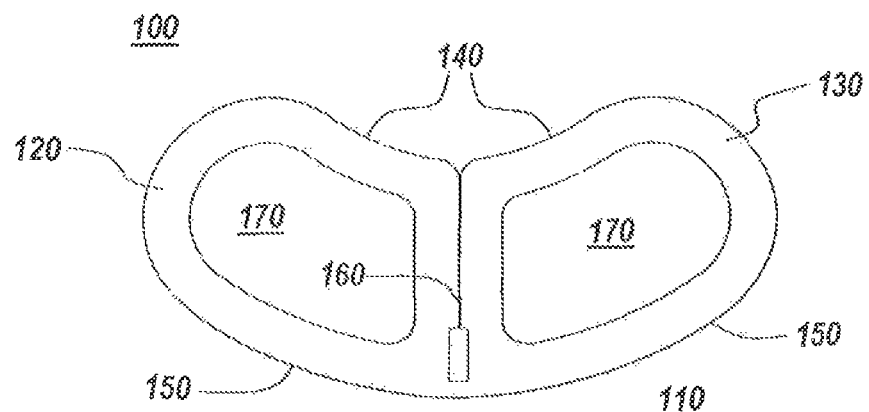
FIG. 1A-1B illustrate one embodiment of an implant having a flexible joint.
Figure 1B:
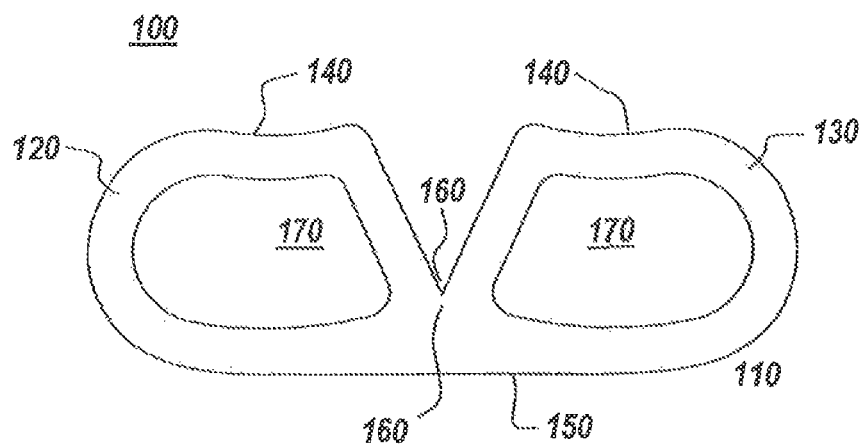

FIGS. 1A and 1B depict one embodiment of an implant 100 for forming a rigid structure between adjoining vertebrae in a patient. In this example the implant comprises a cage 110 having first end 120, second end 130, first side 140, and second side 150 surfaces. The first 140 and second 150 side surfaces extend substantially parallel to each other to span a space between adjoining vertebrae. The first 120 and second 130 end surfaces interconnect said first side surface 140 and second side surface 150. A flexible joint 160 is incorporated into the cage allowing the cage to be deformed for insertion into a patient. FIG. 1A depicts the cage 110 of the implant in a rest state. In this example, the first 140 and second 150 side surfaces are curved giving the cage a curved kidney shape. This curvature and shape provide greater coverage and support then tradition straight-sided implants and is particularly adapted for use in a T-PLIF procedure. While, this shape provides greater biomechanical stability it makes it more difficult to insert and position due to its increased width.

FIG. 1B shows the cage 110 in a deformed state wherein the first side surface 140 has been divided or split at the flexible joint 160 giving the cage a substantially straight-sided profile. This allows the cage implant 100 to be used with traditional insertion devices configured to be used with traditional straight-sided implants.

The cage is designed to provide spacing between adjoining vertebrae while encouraging bone growth. As such, the cage 110 may be formed of any biocompatible material suitable for surgical implantation in a patient. Preferably the cage is form of a polymer or composite through a process such as injection molding. Bio-compatible metals may also be used to add strength or rigidity. Examples of suitable materials include, but are not limited to, PEAK, carbon fiber, titanium, stainless steel, Nitinol, and the like, or any combination thereof.

The cavities 170 created by the cage 110 allow the bone to grow through the cage to fuse the vertebrae. In some embodiments a substance, such as bone chips, or bone graft may be placed in the cavities 170 to encourage bone growth.

In the example of FIGS. 1A and 1B, the flexible joint 160 comprises a living hinge that is formed as part of the cage during the injection molding process. In other embodiments, the joint may not be formed as part of the cage. For example, the cage may comprise two parts that are joined together using a non-unitary joint mechanism that is embedded in or secured to the two parts. Other implementations and embodiments will be apparent to one skilled in the art given the benefit of this disclosure.

Figure 2A:
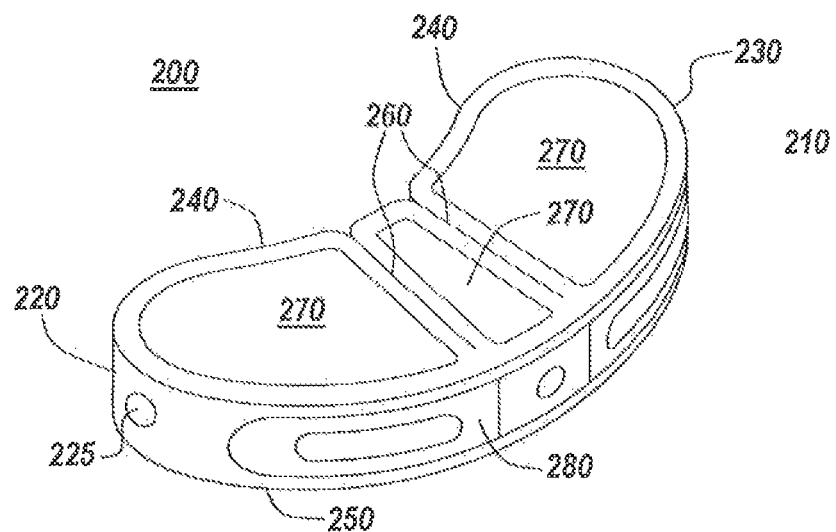
FIG. 2A-2B illustrate another embodiment of an implant a having a number of flexible joints.
Figure 2B:
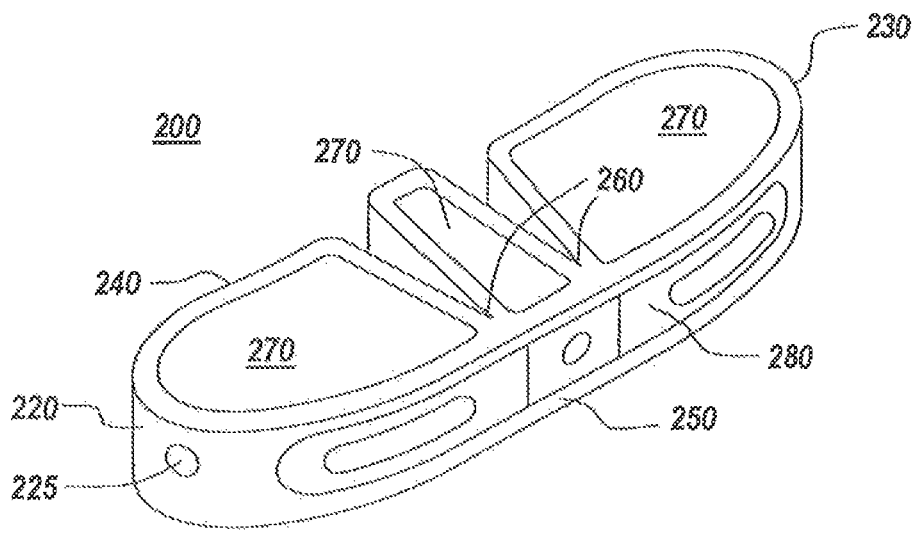

FIGS. 2A and 2B depict another embodiment of the implant 200 of the invention. As with the implant 100 of FIGS. 1A and 1B this implant 200 comprises a cage 210 having first end 220, second end 230, first side 240, and second side 250 surfaces. As in the previous embodiment, the first 240 and second 250 side surfaces are curved and extend substantially parallel to each other to span a space between adjoining vertebrae. The first 220 and second 230 end surfaces interconnect said first side surface 240 and second side surface 250 providing cavities 270 within the cage 210. However, in this embodiment, multiple flexible joints 260 are used to allow the cage to be deformed for insertion into a patient. As with FIG. 1A, FIG. 2A depicts the cage 210 of the implant 200 in a rest state with first 240 and second 250 side surfaces curved to give the cage a curved kidney shape. FIG. 2B shows the cage 210 in a deformed state wherein the first side surface 240 has been divided or split at two flexible joints 160 to give the cage a substantially straight-sided profile.

Similar to the embodiment of FIGS. 1A and 1B, the flexible joints 260 comprise living hinges that are formed as part of the cage during the injection molding process. In this example the flexible joints 260 also include a spring mechanism 280 to reinforce the living hinges and return the cage 210 to a rest state after being deformed. In this example, the spring 280 is formed of a piece of metal attached to the cage. In other embodiments, the spring 280 may be formed of plastic or a composite material. In certain embodiments, the spring 280 may be embedded in the cage 210 during the formation of the cage 210, for example, during injection molding. In other embodiments the spring 280 may be attached to the cage 210 using adhesive, rivets, or other fastening means. In certain embodiments the spring 280 may also serve as the flexible joint 260. Other embodiments and configurations will be apparent to one skilled in the art given the benefit of this disclosure.

The example of FIGS. 2A and 2B also includes an opening 225 in the first end surface 220 for receiving an instrument such as an inserter for attaching the implant to the inserter. In certain embodiments the opening 225 may be in the second end surface 230 or each end surface may have such an opening. Examples of inserters the use of inserters in conjunction with implants can be seen in WO2005077288 A1

Figure 3A:
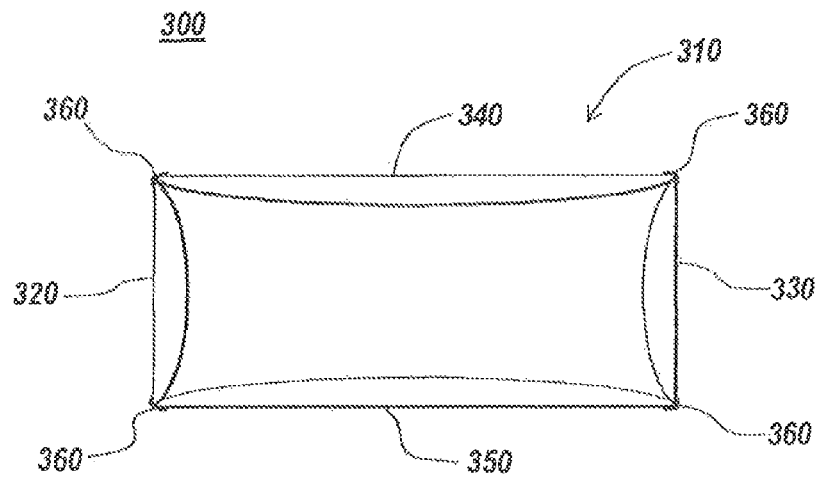
FIGS. 3A-3B illustrate another embodiment of an implant having another type of flexible joint.
Figure 3B:
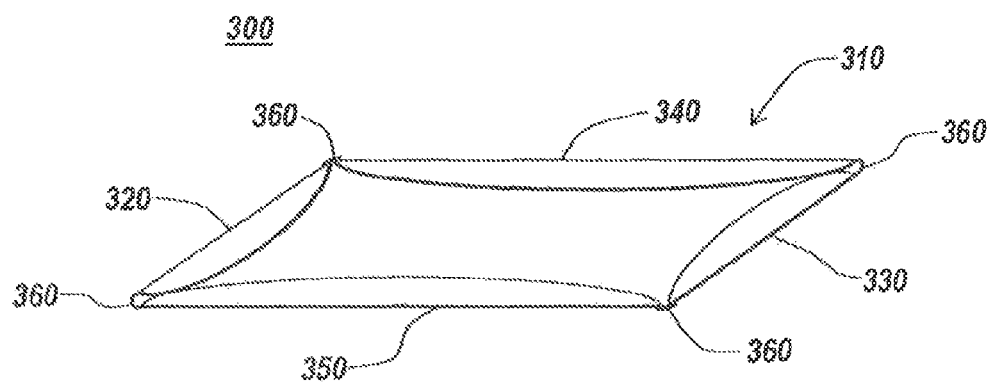

While many of the examples and embodiments discussed in this disclosure focus on curved or kidney-shaped implants, it should be understood that the teaching of the invention are not limited to such shapes. FIGS. 3A-3B depict another example of other possible shapes and flexible joints.

FIGS. 3A and 3B are a top view depicting a straight sided square shaped implant 300. In this example, flexible joints are used to connect the first 340 and second 350 side surfaces to the first 320 and second 330 end surfaces of the cage 310. This allows the cage 310 to be transformed down to a smaller size as shown in FIG. 3B. The ability to transform the cage 310 allows the cage to be inserted through a smaller access port for insertion in between vertebrae.

Figure 4:
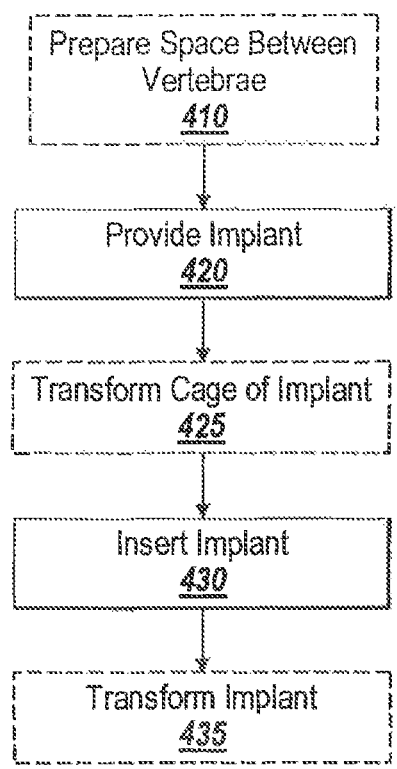
FIG. 4 illustrates a flow diagram for an exemplary embodiment of a method of fusing a spine using the implant of the present invention.

FIG. 4 is a flow chart 400 of an exemplary method for fusing vertebrae of a patient. The method involves substantially the steps of providing an implant of the present invention (step 420) and inserting the implant into the space between adjoining vertebrae in a patient to form a rigid structure between the adjoining vertebrae (step 430).

In some embodiments the method 400 may further include the steps of preparing the space between adjoining vertebrae (step 410) as well as the steps of transforming the cage of the implant to a smaller profile (step 425) before implantation and transforming the cage back to the original profile after insertion (435).

The step of preparing the space between adjoining vertebrae (step 410) may include removing the disk material between the vertebrae. Then the space between the vertebrae may be distracted to relieve pressure from neural elements and provide space for the entry of surgical tools and the insertion of the implant. Preferably the surgery including the insertion is performed using a MIS technique such a T-PLIF procedure.

Because MIS techniques such as T-PLIF procedures use a more limited access port or window, the cage of the implant may need to be transformed or otherwise deformed in order to fit through the access port or window (step 425) and be positioned in the space between vertebrae. Once in position, the cage may then be transformed back or otherwise returned to its rest state (step 435). In certain embodiments this is performed by a spring incorporated or attached to the one or more flexible joints.

In some embodiments, the implant 500 may further include surface configurations 590 on at least one of the first 540 and second 550 side surfaces of the cage 510 for slidably attaching the implant 500 to an insertion guide. An example of this can be seen in FIGS. 5A and 5B. Here the surface configurations 590 are tabs or fingers formed on the first side surface 540. When used in conjunction with an insertion guide, the flexible joints 560 of the implant 500 allow the cage 510 to deform (i.e. straighten) to conform to the shape of the insertion guide. This is described in more detail below.

Figure 5A:
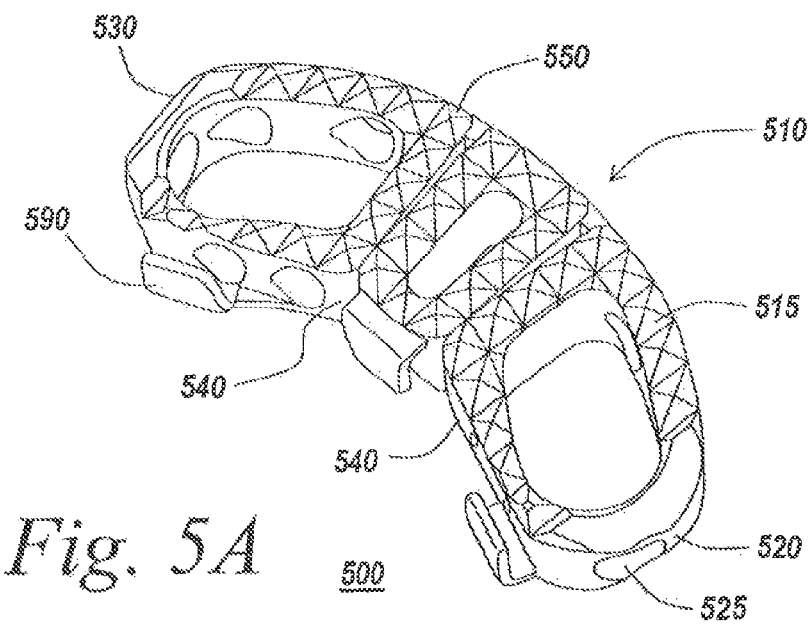
FIG. 5A-5B illustrate another embodiment of an implant having a number of flexible joints and surface configurations.
Figure 5B:
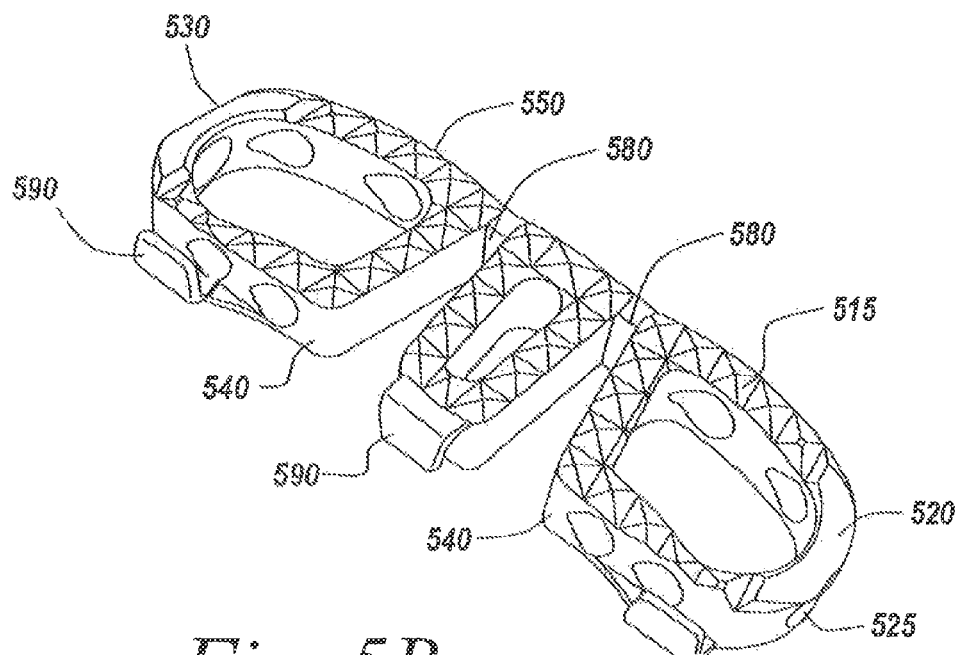

In the embodiments of FIGS. 5A and 5B, the cage 510 further includes textured edges 515 on the first end 520, second end 530, first side 540, and second side 550 surfaces for engaging the bone of the adjoining vertebrae to secure the implant in place in the space between vertebrae. Other possible configurations and textures for securing the implant 500 will be apparent to one skilled in the art given the benefit of this disclosure.

Figure 6:
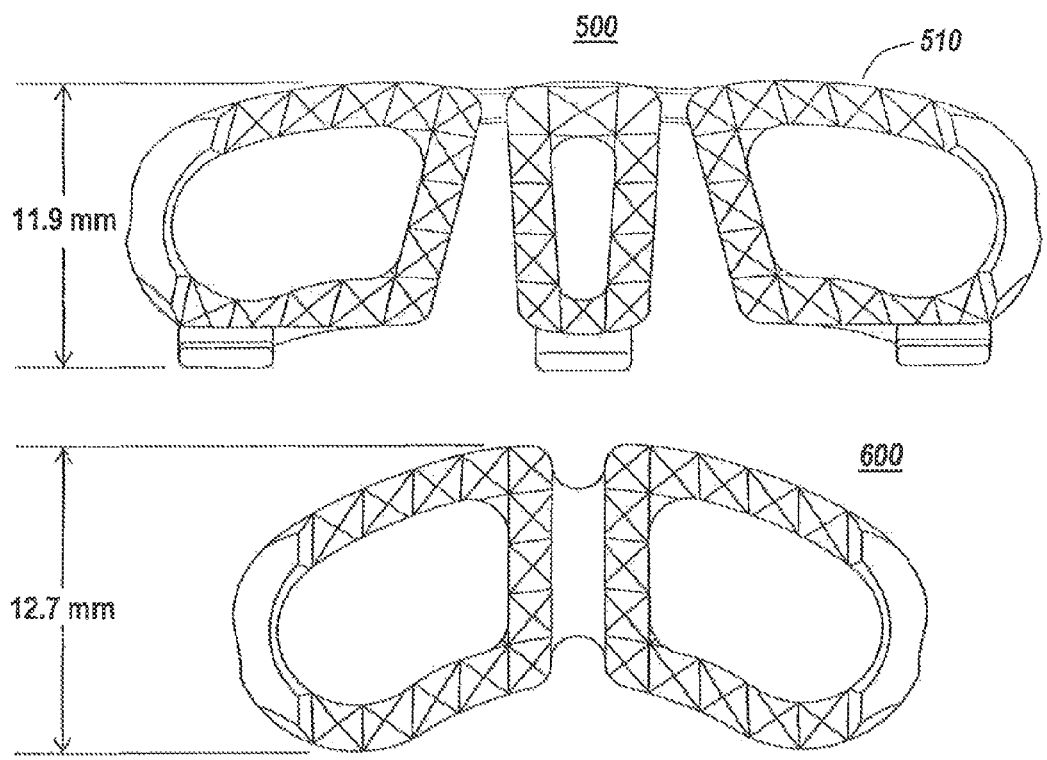
FIG. 6 illustrates the deformable nature of the implant of the present invention.

FIG. 6 depicts one advantage of the cage 510 of the implant being able to deform. The ability of the implant 500 of the present invention to deform allows the profile of the cage to be transformed to a smaller profile. When thus transformed, the implant can be passed through a passage smaller than what is required by a traditional curved implant 600. As shown here, the deformed (compressed) implant 500 (including surface configurations) requires only 11.9 mm of space as opposed to the 12.7 mm of space required for a fixed, non-deformable, curved implant 600 of the same size.

In another embodiment of the present invention, a system is provided for forming a rigid structure between adjoining vertebrae in a patient. An example of such a system can be seen in FIG. 7. The system 700 includes an implant 500 of the present invention as shown in FIGS. 5A and 5B having surface configurations 590 for slidably attaching the implant 500 to an insertion guide 710. As shown in this embodiment, the flexible joints 560 of the implant may allow the cage 510 to conform to the shape of the insertion guide 710. In this case the cage 510 is deformed so as to have a smaller straight-sided profile when attached to a straight portion of the insertion guide 710.

Figure 7:
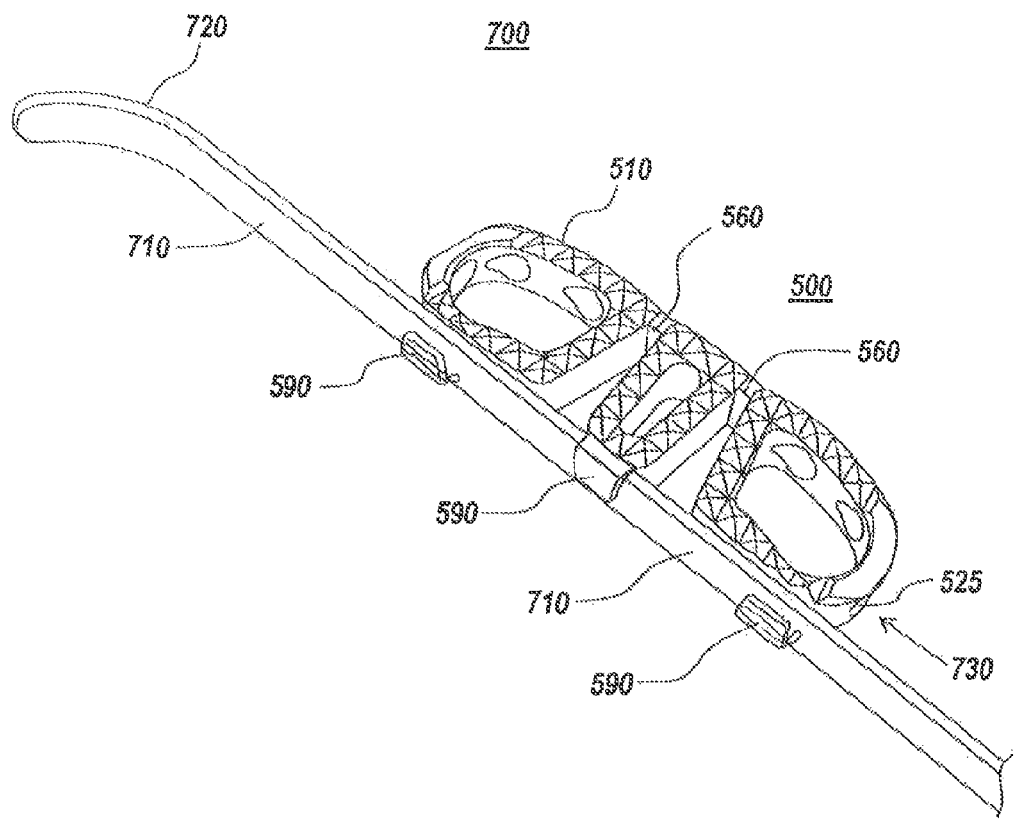
FIG. 7 illustrate an embodiment of the system of the present invention wherein the implant has surface configurations that slidably attach the implant to an insertion guide.

In certain embodiments, such as shown in FIG. 7, the insertion guide 710 may have a curved end 720 to further assist in the insertion and positioning of the implant 510. In use, when the implant is slid along the insertion guide 710 in the direction of arrow 730, the flexible joints 560 of the implant 500 allow the implant to curve to conform to the curved end 720 of the insertion guide 710. The implant 500 may slide along the insertion guide 710 using an inserter configured to mate with opening 525.

Figure 8:
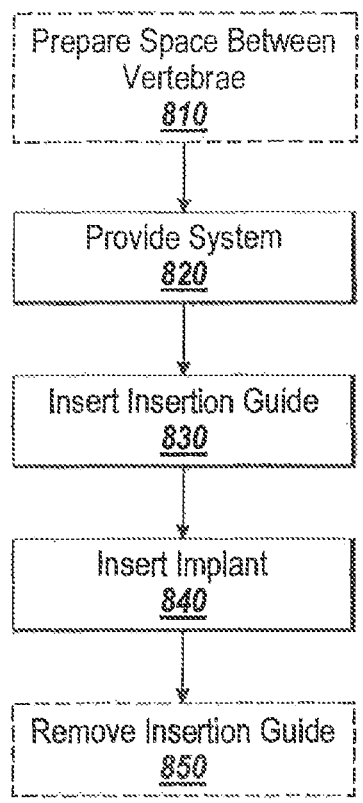
FIG. 8 illustrates a flow diagram for an exemplary embodiment of a method of fusing a spine using the system of the present invention

FIG. 8 is a flow chart 800 of an exemplary method for fusing vertebrae of a patient. The method involves substantially the steps of providing a system of the present invention having an implant with surface configurations and an insertion guide (Step 820), inserting the insertion guide into the space between adjoining vertebrae (Step 830), and sliding the implant along the length of the insertion guide to position the implant in the space between adjoining vertebrae, (Step 840).

In some embodiments the method 800 may further include the steps of preparing the space between adjoining vertebrae (Step 810) as well as the step of removing the insertion guide after the implant has been inserted (Step 850).

The step of preparing the space between adjoining vertebrae (Step 810) may include removing the disk material between the vertebrae. Then the space between the vertebrae may be distracted to relieve pressure from neural elements and provide space for the entry of surgical tools and the insertion of the implant. Preferably the surgery including the insertion is performed using a MIS technique such a T-PLIF procedure.

Figure 9A:
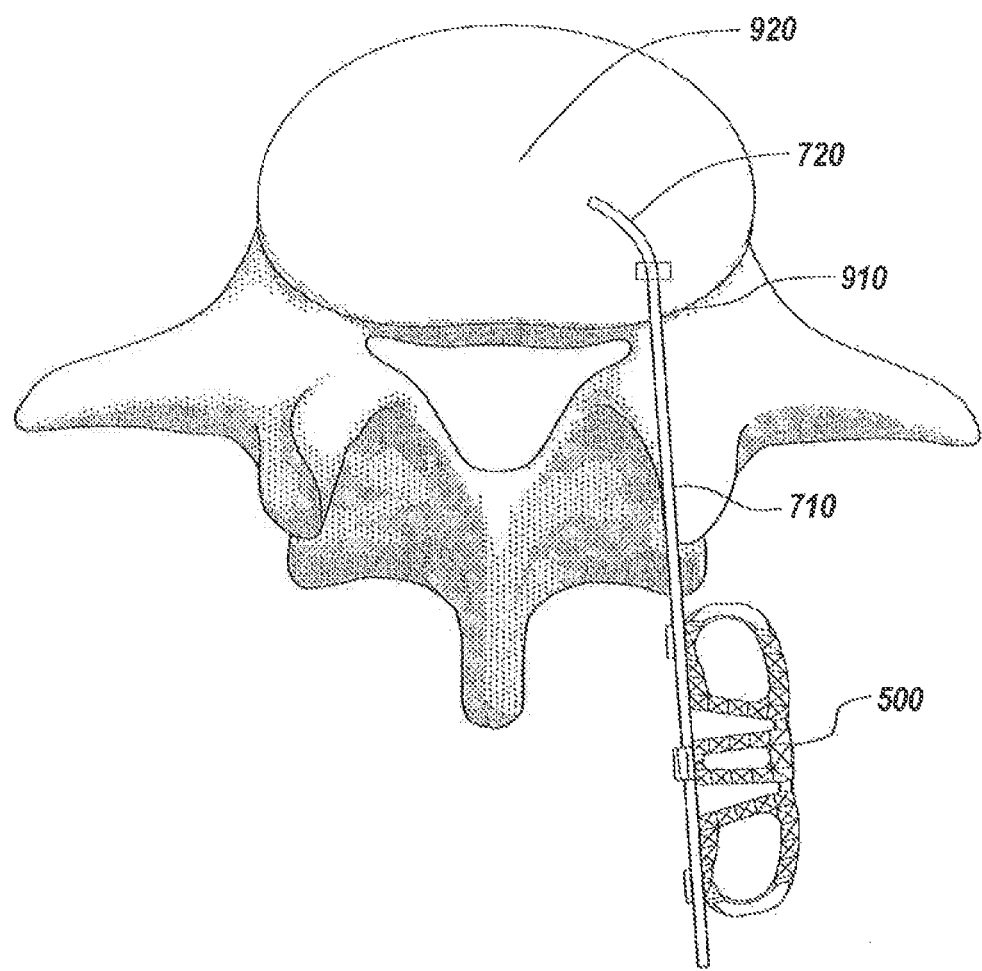
FIGS. 9A-9D illustrate one embodiment of how the implant of the system of the present invention is inserted by sliding the implant along the insertion guide as set forth in the exemplary embodiment of the method of FIG. 8.

Examples of this methodology using a T-PLIF technique can be seen in FIG. 9A-D. Because MIS techniques such as T-PLIF procedures use a more limited access port or window 910, the insertion guide with a curved tip 720 is used to deform and guide the implant 500 so as to be inserted into and positioned in the space 920 between vertebrae as seen in FIG. 9A.

Figure 9B:
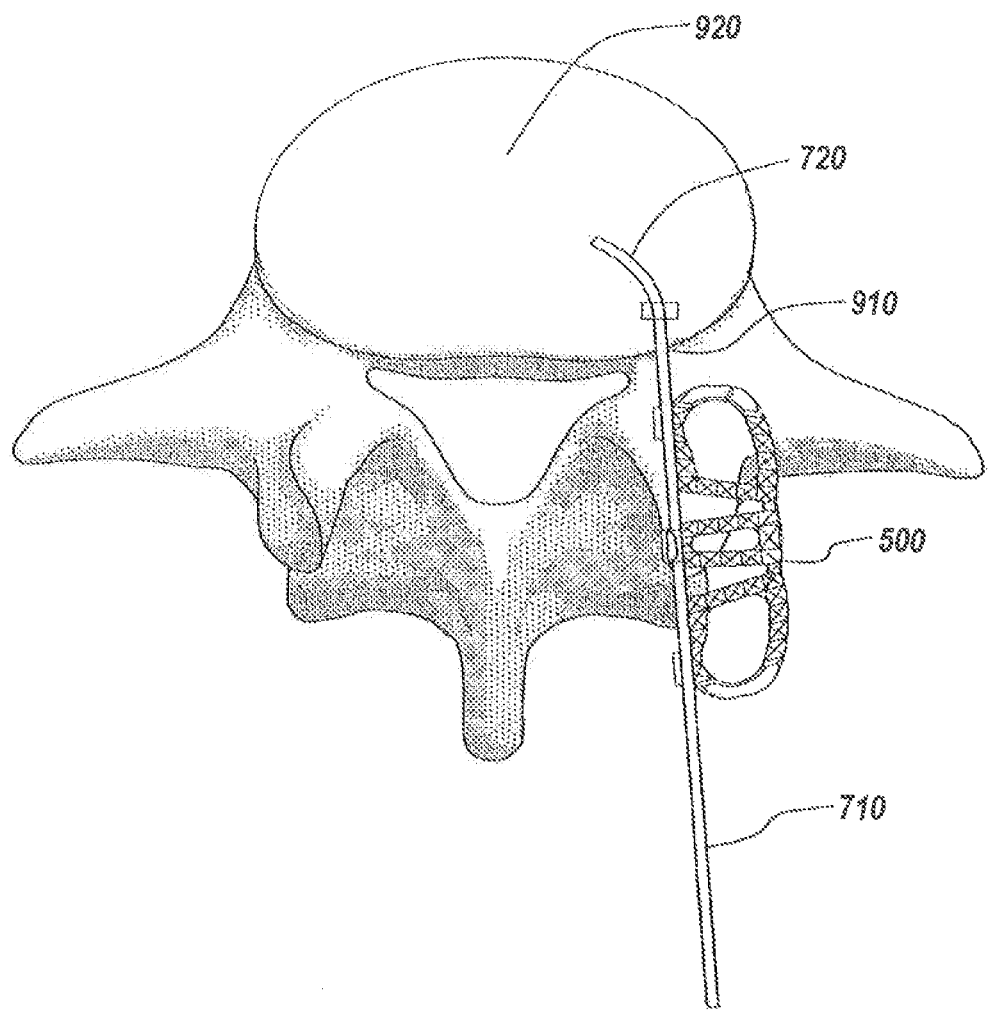

In FIG. 9B, the implant is slid along the length of the insertion guide 710. The implant 600 may be slid along the insertion guide 710 using an insertion tool (not shown) mated with the opening 525 configured to receive the insertion tool. Examples of suitable insertion devices and their use is discussed in WO2005077288 A1.

Figure 9C:
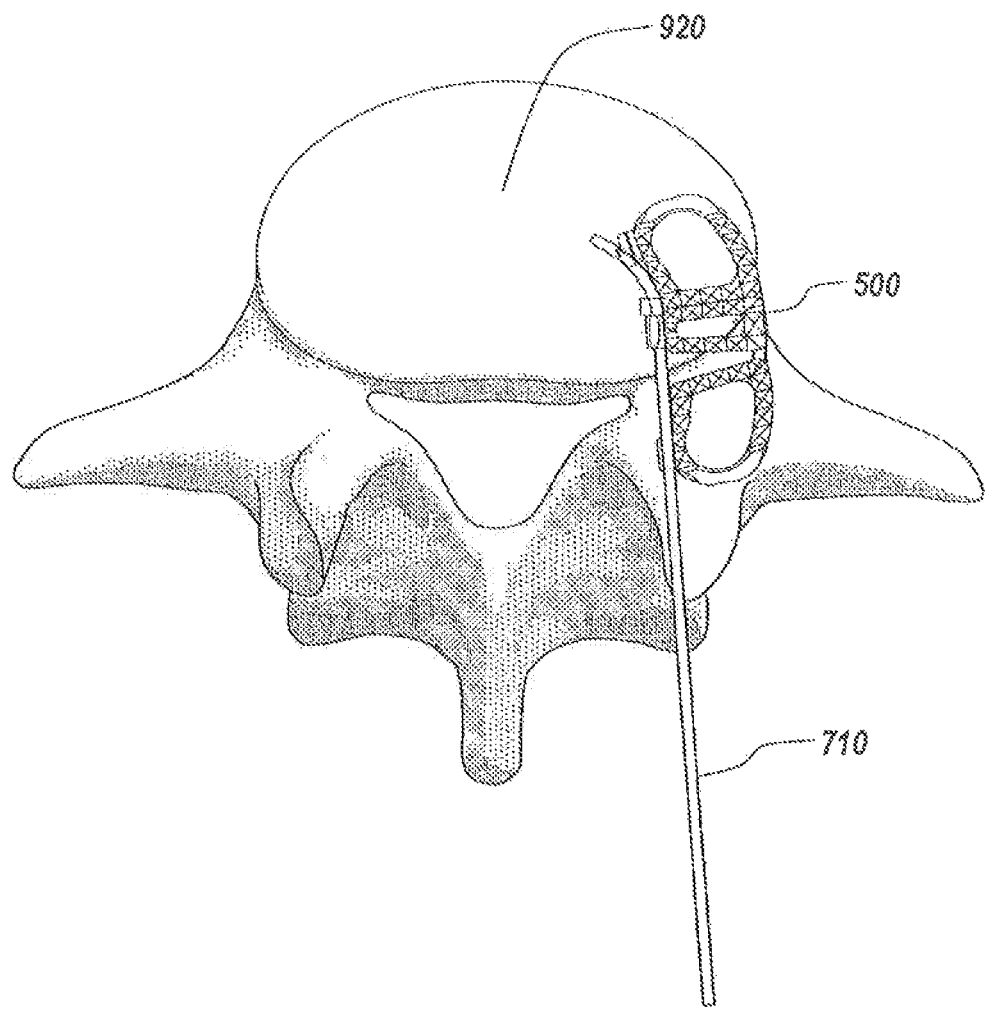

In FIG. 9C, the insertion guide 710 is used to guide the implant 500 through the access window 910 and position the implant in location in the space 920 between vertebrae. The use of the curved tip 720 allows the implant 510 to be positioned at a desired angle, preferably around 45°, even though the angle of approach through the access window 910 may be closer to 350°.

Figure 9D:
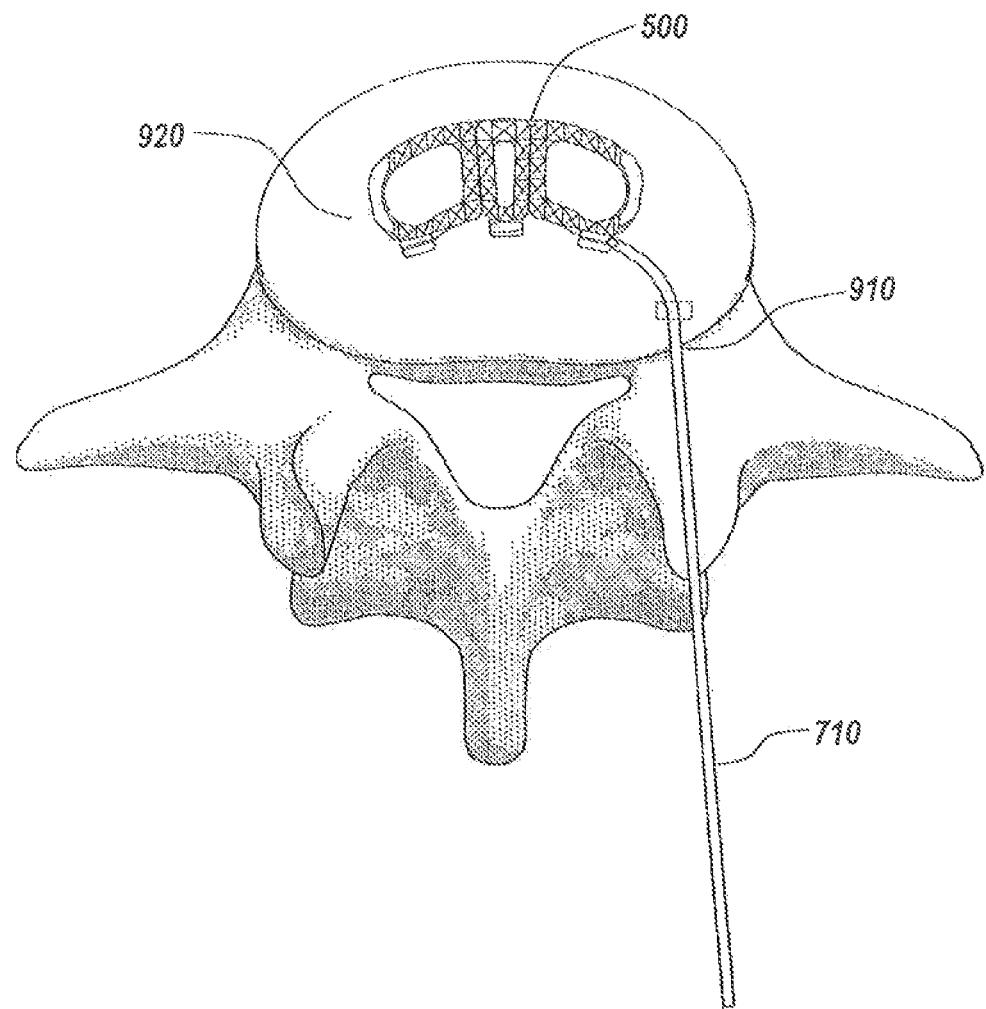

Once in position, the insertion guide 710 may be removed and the implant allowed to transform or otherwise return to its rest state as seen in FIG. 9D. In certain embodiments this is performed by a spring incorporated or attached to the one or more flexible joints.

The apparatus and techniques of the present invention provide numerous advantages. The implant of the present invention can be used in minimally invasive surgery (MIS) wherein the cage can be deformed for easier insertion and positioning through a smaller access port. In certain embodiments, the cage may have surface configurations for use with an insertion guide. The cage of the implant can be deformed to conform to the shape of the guide which allows for curved guides which in turn provide more accurate insertion and positioning.

Although, the present invention has been described relative to an illustrative embodiment and application in spinal correction surgery. It should be apparent that the present invention may be used in any number of surgical procedures. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A surgical method comprising:
    inserting a guide into a space between adjacent vertebrae; and
    advancing a cage along the guide, the cage having one or more flexible joints that allow the cage to move between a curved configuration and a straight configuration;
    wherein as the cage is advanced along the guide, the cage conforms to a curved portion of the guide such that the cage moves from the straight configuration to the curved configuration.

2. The method of claim 1, wherein the one or more flexible joints allow the cage to conform to a shape of the guide as the cage is advanced along the guide.

3. The method of claim 1, wherein the cage is advanced along the guide via one or more projections on the cage that couple to the guide.

4. The method of claim 1, wherein the cage is advanced along the guide via an inserter instrument coupled to an opening in a first end of the cage.

5. The method of claim 1, further comprising removing disc material from the space between the adjacent vertebrae.

6. The method of claim 1, further comprising distracting the space between the adjacent vertebrae before inserting the guide therein.

7. The method of claim 1, wherein when the cage is positioned in the space between the adjacent vertebrae, the cage is in the curved configuration.

8. The method of claim 1, further comprising placing bone growth material in the cage prior to inserting the cage into the space between the adjacent vertebrae.

9. The method of claim 3, wherein the cage slides along the guide via the one or more projections.

10. The method of claim 3, wherein the one or more projections project out of at least one of first and second surfaces of the cage.

11. A surgical method comprising:
    inserting an implant into a space between first and second vertebrae, the implant having:
    superior and inferior surfaces,
    first and second end surfaces,
    first and second lateral surfaces, and
    at least one joint that allows the implant to move from an insertion configuration in which the first and second lateral surfaces are substantially parallel to a deployed configuration in which the first and second lateral surfaces are curved;
    wherein as the implant is inserted into the space between the first and second vertebrae, the first end surface follows a curved path along a curved guide and the implant moves from the insertion configuration to the deployed configuration.

12. The method of claim 11, wherein the implant includes first and second mating features formed on opposite sides of the at least one joint.

13. The method of claim 11, further comprising forming a transforaminal window to access the space between the first and second vertebrae and inserting the implant therethrough.

14. The method of claim 13, wherein an axis extending through the transforaminal window is disposed at an angle of around 45 degrees relative to an anterior-posterior axis of the vertebrae.

15. The method of claim 13, wherein an axis extending through the transforaminal window is disposed at an angle of around 35 degrees relative to an anterior-posterior axis of the vertebrae.

16. The method of claim 11, further comprising placing bone growth material in the implant.

17. A surgical method, comprising:
    forming a window that provides access to an intervertebral space;
    positioning an implant having at least superior and inferior surfaces, first and second lateral surfaces, and first and second ends in a first configuration in which the first and second lateral surfaces are substantially straight;
    passing the implant through the window and into the intervertebral space in the first configuration at least partially along a guide; and
    transforming the implant without retracting the guide to a second configuration in which the first and second lateral surfaces have a curved shape and a first portion of the implant is positioned on a first side of an anterior-posterior axis of the space and a second portion of the implant is positioned on a second side of the anterior-posterior axis.

18. The method of claim 17, wherein the window comprises a transforaminal window formed on a posterior side of vertebrae that defines the intervertebral space.

19. The method of claim 18, wherein an axis extending through the transforaminal window is disposed at an angle of around 45 degrees relative to an anterior-posterior axis of the vertebrae.

20. The method of claim 18, wherein an axis extending through the transforaminal window is disposed at an angle of around 35 degrees relative to an anterior-posterior axis of the vertebrae.

21. The method of claim 17, wherein the implant includes a spring mechanism that biases the implant to the second configuration.

* * * * *